United States Patent [19]

Kuk et al.

[11] Patent Number: 5,077,441

[45] Date of Patent: Dec. 31, 1991

[54] SELECTIVE GOSSYPOL ABATEMENT PROCESS FROM OIL EXTRACTION OF COTTONSEED

[75] Inventors: Myong S. Kuk, Metairie; Robert J. Hron, Sr., New Orleans; George Abraham, Metairie, all of La.

[73] Assignee: The United States of America as represented by the Secretary of Agriculture, Washington, D.C.

[21] Appl. No.: 593,174

[22] Filed: Oct. 5, 1990

[51] Int. Cl.$^5$ .................... C07C 37/68; C07C 45/90
[52] U.S. Cl. .................................. 568/761; 568/438; 568/724
[58] Field of Search ............... 568/717, 718, 722, 723, 568/724, 730, 761, 438

[56] References Cited

U.S. PATENT DOCUMENTS

| | | | |
|---|---|---|---|
| 4,062,882 | 12/1977 | Sen Gupta | 260/423.5 |
| 4,100,203 | 7/1978 | Rutledge | 568/730 |
| 4,144,229 | 3/1979 | Kornofsky | 260/123.5 |
| 4,356,331 | 10/1982 | Inoue | 568/758 |
| 4,375,568 | 3/1983 | Izod et al. | 568/758 |
| 4,987,273 | 1/1991 | Bitter et al. | 568/758 |

FOREIGN PATENT DOCUMENTS

| | | | |
|---|---|---|---|
| 0370555 | 5/1990 | European Pat. Off. | 568/758 |
| 0045430 | 4/1981 | Japan | 568/758 |
| 4003133 | 1/1989 | Japan | 568/761 |

OTHER PUBLICATIONS

A. K. Sen Gupta, "Neuere Entwicklungen auf dem Gebiet der Raffination der Speiseole," Fette Seifen Anstrichmittel 88(3): 79–86 (1986) [English summary].
Akio Iwama, "Membrane Separation Process for Soybean Oil Refining and Its Economical Effects", Membrane 11(2): 99–108 (1986) [English summary].
J. T. Lawhon et al., "Processing Whey-Type By-Product Liquids from Cottonseed Protein Isolation with Ultrafiltration and Reverse Osmosis Membranes", Journal of Food Process Engineering 1: 15–35 (1977).
W. D. Harris et al., "Isopropanol as a Solvent for Extraction of Cottonseed Oil. I. Preliminary Investigations", Journal of the American Oil Chemists' Society 24: 370–375 (1947).
R. K. Rao and L. K. Arnold, "Alcoholic Extraction of Vegetable Oils. V. Pilot Plant Extraction of Cottonseed by Aqueous Ethanol", Journal of the American Oil Chemists' Society 35: 277–281 (1958).

*Primary Examiner*—Werren B. Lone
*Attorney, Agent, or Firm*—M. Howard Silverstein; Randall E. Deck; John D. Fado

[57] ABSTRACT

A method for the treatment of plant material to provide a protein-rich product and oil relatively free of gossypol. The process includes the steps of:

a. contacting plant material with an aqueous monohydric alcohol solvent to extract oil and gossypol from the plant material and form a miscella fraction including the solvent, oil and gossypol, and a plant material fraction having gossypol removed therefrom;

b. separating the solvent from the oil and gossypol in the miscella, preferably by membrane separation under pressure in a membrane separation unit, to form a first (retentate) fraction comprising the oil and gossypol, and a second (permeate) fraction comprising the solvent; and c. contacting the first fraction with an adsorbent effective to separate the gossypol from the oil therein.

The plant material and oil remaining after the process are relatively free of gossypol and may be recovered for subsequent use. The plant material is especially valuable as a protein-rich food product or feed.

18 Claims, No Drawings

SELECTIVE GOSSYPOL ABATEMENT PROCESS FROM OIL EXTRACTION OF COTTONSEED

BACKGROUND OF THE INVENTION

1. Field of the Invention

The invention relates to a method for the treatment of plant material to provide a protein-rich product and oil relatively free of gossypol.

2. Description of the Prior Art

Gossypol is a known poisonous pigment found in plant material such as cottonseed and has been the object of prior schemes for removal therefrom. Previous attempts to remove gossypol from cottonseed products have included extraction with non-aqueous organic solvents such as hexane and other petroleum fractions, and/or with aqueous monohydric alcohols such as ethanol and isopropyl alcohol.

Sen Gupta [U.S. Pat. Nos. 4,062,882 and 4,533,501] and Iwama [*Membrane*, vol. 11, no. 2 (1986), pp. 99–108] described desliming processes for the removal of phospholipids from cottonseed and other vegetable oils by extraction with non-aqueous, non-alcoholic organic solvents such as hexane. According to the disclosed processes, the oil was contacted with the solvent to form a miscella, from which the phospholipids therein could be separated by reverse osmosis or ultrafiltration yielding a retentate stream containing the phospholipids, and by a permeate stream of the oil and solvent. In later work, Sen Gupta et al. [*Fette Seifen Anstrichmittel*, vol. 88, no. 3 (1986), pp. 79–86] disclosed that gossypol could be removed with the phospholipids by substantially the same process.

Lawhon et al. [*Journal of Food Process Engineering*, vol. 1 (1977), pp. 15–35] disclosed processes for the recovery of residual protein from cottonseed wheys. In the course of protein isolation from dry cottonseed flour by contacting with water, a cottonseed whey was obtained containing residual proteins in addition to smaller molecular weight components (i.e., carbohydrates, salts, amino acids and short-chain peptides). The content of oil and gossypol in the whey was described as negligible.

Ultrafiltration of the whey yielded a retentate stream containing the protein, and a permeate stream which, when subsequently subjected to reverse-osmosis, yielded a retentate stream of the smaller molecular weight components and a permeate stream of water.

As mentioned above, the use of aqueous monohydric alcohol solvents has also been described in the prior art for the extraction of gossypol and/or oil from cottonseed as, for example, in Karnofsky [U.S. Pat. No. 4,144,229], Harris et al. [*Journal of the American Oil Chemists' Society*, vol. 24 (1947), pp. 370–375], or Rao et al. [*JAOCS*, vol. 35 (1958), pp. 277–281]. Although each of the references described the formation of a miscella composed of the oil, solvent, and gossypol after extraction of the cottonseed flakes with the solvent, the components of the miscella were separated by phase separation, liquid/liquid extraction, or evaporation. The prior art did not disclose the use of reverse-osmosis and selective adsorption for the separation of these components of the miscella.

SUMMARY OF THE INVENTION

We have now invented a method for the treatment of plant material to provide a protein-rich product and oil relatively free of gossypol and gossypol-like components. The process includes the steps of:

a. contacting plant material with an aqueous monohydric alcohol solvent to extract oil and gossypol from the plant material and form a miscella fraction including the solvent, oil and gossypol, and a plant material fraction having gossypol removed therefrom;

b. separating the solvent from the oil and gossypol in the miscella, preferably by membrane separation under pressure in a membrane separation unit, to form a first (retentate) fraction comprising the oil and gossypol, and a second (permeate) fraction comprising the solvent; and c. contacting the first fraction with an adsorbent effective to separate the gossypol from the oil therein.

The plant material and oil remaining after the process are relatively free of gossypol and and gossypol-like compounds and may be recovered for subsequent use. The plant material is especially valuable as a protein-rich food product or feed.

In accordance with this discovery, it is an object of this invention to provide a method for removing gossypol from plant material yielding a protein-rich product and oil relatively free of gossypol. In particular, it is an objective to provide a process for removing gossypol from cottonseed.

DETAILED DESCRIPTION OF THE INVENTION

According to the process of the invention, the plant material is contacted with an aqueous monohydric alcohol solvent for a sufficient time and at an effective temperature to extract oil and gossypol therefrom and results in the formation of a miscella fraction which includes the solvent, oil, and gossypol (as well as gossypol-like compounds), and a plant material fraction having gossypol removed therefrom. After the extraction, the remaining plant material is relatively free of gossypol and may be recovered for subsequent use. The miscella is transferred to a separation unit wherein the solvent is separated from the oil and gossypol. This separation of the solvent is preferably achieved by membrane separation of the miscella under pressure in a membrane separation unit. This separation yields a first (retentate) fraction including at least a substantial or major portion of the oil and gossypol, and a second (permeate) fraction including at least a substantial or major portion of the solvent. This separation step may be repeated to produce either permeate or retentate streams of desired compositions. The second fraction containing solvent is advantageously recycled for use in the extraction of fresh plant material. The first fraction is contacted with an adsorbent effective to separate the gossypol and gossypol-like compounds from the oil, providing an oil stream which is also relatively free of gossypol and may be recovered for subsequent use. Used adsorbent may be regenerated for treatment of additional plant material. The process may be conducted in batch or continuous mode.

Any gossypol-containing plant material may be treated for the removal of gossypol therefrom. The process is particularly useful in the treatment of cottonseed and products therefrom. In preparation for such treatment, the plant material is preferably mechanically or otherwise processed, such as by grinding, flaking, or extruding, to enhance contact of the gossypol therein with the solvent described above. Although not essential, the moisture content of the plant material may also be adjusted at this time, within the range of about 2 to 12% by weight.

Contact of the solvent with the plant material for the extraction of oil and gossypol may be achieved using leaching or extracting equipment conventional in the art, operating in batch or continuous mode. In the preferred embodiment, this step utilizes counter-current or co-current systems, such as shallow-bed or bucket type extractors. Suitable operating conditions for the extraction may be readily selected by the practitioner skilled in the art. The extraction may be conducted at a single temperature in a single contactor or a plurality of contactors. However, in the preferred embodiment, the plant material is either contacted with solvent in a single contacting device operating with two different temperature regions, or contacted in two contacting devices each operating at a different temperature. It is preferred that the initial contact temperature (or single temperature if only one is used) be maintained below about 60° C. to minimize bonding of the gossypol to proteins in the plant material. The final contact temperature, if two stages are used, is controlled between about 60° C. and the normal boiling point of the miscella. The solvent employed may be any aqueous monohydric alcohol solvent, and is advantageously selected from lower monohydric alcohols such as isopropyl alcohol, propyl alcohol, ethanol, methanol, or mixtures thereof. The ratio of the solvent to the plant material will vary with the plant material treated and its oil and gossypol content. In the preferred embodiment for the treatment of cottonseed, the ratio is between about 1:1 and 10:1 by weight.

Upon completion of the extraction of the oil and gossypol into the solvent, the miscella is transferred to the separation unit for separation of the solvent from the oil and gossypol. This transfer is preferably conducted under adiabatic conditions with the temperature maintained between about 60° C. and ambient temperature. The temperature of the miscella during the transfer may vary with the composition thereof, and is advantageously maintained above its critical solution temperature to ensure that the miscella remains as a single phase, and does not split into an oil-rich phase and a solvent-rich phase. However, in the event of phase splitting, the two phases are each treated independently for the separation of solvent from oil and gossypol as described below, each in the same manner as if phase splitting did not occur. During this transfer step, the miscella may be passed through one or more sieves, with standard sieve numbers between about 80 and 200, for the removal of fine particles of plant material therefrom.

In the alternative to directly transferring the miscella from the extraction to the separation unit as described above, the withdrawn miscella or a portion thereof may be recycled. This would be especially applicable to those instances where the gossypol content of the miscella exiting the extraction or leaching equipment was relatively low.

Separation or removal of the solvent from the oil and gossypol in the miscella is preferably achieved by membrane separation of the miscella under pressure, particularly by reverse osmosis or ultrafiltration. In this embodiment, the separation would employ a membrane separation unit. The structure of this membrane separation unit is not critical and may include reverse-osmosis membrane systems or ultrafiltration systems conventional in the art. The membranes of the membrane separation unit are semi-permeable and their porosity is selected to allow passage of the solvent but not oil or gossypol. Preferably, the membranes have molecular weight cut-offs between about 500 and 2,000 daltons, especially below about 1,500 daltons. Flow through the membrane separation unit may be turbulent and parallel to the surface of the membrane for enhanced contact of the miscella therewith. The pressure in the unit will vary with the membrane selected and may be up to about 1,000 psia.

In the alternative to membrane separation under pressure, the practitioner skilled in the art will recognize that other separation techniques may be employed for the separation of solvent from oil and gossypol. Such alternatives may include, but are not limited to, evaporation, vacuum distillation, or dialysis.

As referred to above, the solvent in the collection of second or permeate fractions obtained from the separation is preferably recycled for use in extracting fresh plant material. Recycling in this manner allows for improved removal of gossypol from the plant material, while minimizing the amount of solvent required. Without wishing to be bound by theory, when contacted with suitable solvent, gossypol from the plant material exists in an equilibrium between the plant material solid phase and the miscella or solvent phase. The concentration of gossypol in the plant material can be reduced by lowering the concentration of the gossypol in the miscella or solvent. This lowering of the gossypol concentration in the solvent and, consequently, in the solid phase is achieved by the above-described steps of removing the miscella, and separating and recycling the solvent therefrom. Prior to recycling, the solvent in the second fraction may by further purified to remove any residual oil or contaminants, using the same or different techniques described for the separation of the solvent from the miscella described above.

The separation of the miscella also yields a first or retentate fraction of concentrated gossypol and oil, from which gossypol can be further separated by contact with a selective adsorbent, to provide a vegetable oil relatively free of gossypol. This latter separation is achieved by contacting the collection of first fractions with an absorbent effective for the selective removal of gossypol therefrom. Suitable adsorbents may be selected by the skilled practitioner in the art, and include but are not limited to alumina, silica, or polymeric adsorbents. Used adsorbents may be regenerated using techniques known in the art, for example, by washing with ketones such as acetone or methylethyl ketone, followed by treatment with sodium hypochlorite solution.

Conducting the step of separation of the solvent from the miscella before the step of adsorption of gossypol as described above provides the advantage of reducing the volume of the feed stream into the adsorption units or columns. This in turn minimizes the size of the adsorption column required. However, it is understood that the order of these steps could be reversed. In this event, the miscella resulting from the extraction of the plant material with solvent is contacted with an adsorbent effective to remove gossypol as described above, and results in a filtrate stream of the oil and solvent. The filtrate stream may then be treated for the separation of the solvent therefrom in the same manner as described above, resulting in the formation of an oil fraction and a solvent fraction.

EXAMPLE 1

Dehulled and moisture-conditioned cottonseed in flaked form was contacted with 95% ethanol in a pilot-scale Crown extractor at a temperature below the normal boiling point of 95% ethanol, generating a miscella fraction and a cottonseed meal fraction. To demonstrate the effectiveness of the inventive process, 250 ml of lean miscella was spiked with pure gossypol to raise the gossypol concentration to about 621.7 ppm. This spiked miscella was placed under 60 psig head pressure at ambient temperature in an Amicon membrane-stirring cell. The membranes used in this example were anisotropic, polyamide membranes with nominal molecular weight cut-off values between 500 and 1500 daltons. The miscella solution in the cell was stirred by vigorously rotating a rod-type stirrer placed about 1 mm above the membrane surface, using a magnetic rotator. This stirring resulted in a turbulent flow uniformly sweeping across the membrane surface. In this operation, the solvent molecules readily pass through the membrane, while most of the glyceride oil and gossypol are retained. About 185 ml of the gossypol-containing retentate was recovered, having a gossypol content of about 1108 ppm.

For the adsorption of gossypol from the miscella, trials were run comparing two adsorbents: silica and alumina. In the first column, 20 g of silica with a grain size between 60 and 200 mesh was gently packed by tapping and gravity into a glass column with an ID of 25 mm and a length of 30 cm. A second column of identical size and shape was packed in the same manner with 20 g of alumina having a grain size between 80 and 200 mesh. Fifty milliliters of the retentate obtained above was introduced into each column at ambient temperature, and filtrate was collected by gravity. The columns were under a nitrogen blanket at pressures ranging from atmospheric, 15 psia, or 20 psia. The content of the gossypol in the filtrate was determined by HPLC and is shown in Table I.

TABLE I

| Stream | Gossypol Content (ppm) |
|---|---|
| feed (miscella) | 1108.2 |
| filtrate (silica adsorbent @ atmospheric P) | 1.89 |
| filtrate (alumina adsorbent @ 20 psia) | 1.59 |
| filtrate (alumina adsorbent @ 15 psia) | none |

After completion of the adsorption, the columns were regenerated. Adsorbed gossypol was eluted by washing the column with acetone, followed by methylethyl ketone. After drying in vacuo, the column was treated with 5.25% sodium hypochlorite to complete regeneration. The wash solvents may or may not be combined, and may be recovered by evaporation, leaving a crude gossypol fraction.

EXAMPLE 2

A separate trial was conducted in order to demonstrate the effectiveness of the adsorbent in separating gossypol even from feed streams containing solvent, as in the event of reversing the order of the solvent separation and adsorption steps. A simulated miscella was prepared by combining ethanol with gossypol and the cottonseed glyceride components such as triolein and trilinolein. This miscella was contacted with the alumina adsorbent in the same manner as in Example 1. The filtrate recovered contained substantially no gossypol, and substantially all of the solvent and oil components. The content of gossypol in the feed and filtrate was determined by HPLC and is shown in Table II.

TABLE II

| Stream | Gossypol Content (ppm) |
|---|---|
| feed | 749.8 |
| filtrate (@ 15 psia) | 1.32 |
| filtrate (@ 20 psia) | 1.39 |

It is noted that the foregoing detailed description is given merely by way of illustration and that modifications and variations may be made therein without departing from the spirit and scope of the invention.

We claim:

1. A process for the removal of gossypol from plant material comprising the steps of:
   a. contacting plant material with an aqueous monohydric alcohol solvent to extract oil and gossypol from the plant material and form a miscella fraction comprising said solvent, oil, and gossypol, and a plant material fraction having gossypol removed therefrom;
   b. separating said solvent from said oil and gossypol in a separation unit to form a first fraction comprising said oil and gossypol, and a second fraction comprising said solvent; and
   c. contacting said first fraction with an adsorbent effective to separate said gossypol from said oil in the first fraction.

2. The process as described in claim 1, wherein said step of separating is by membrane separation of said miscella under pressure forming a retentate fraction and a permeate fraction, and said first fraction comprises the retentate fraction, said second fraction comprises the permeate fraction, and said separation unit comprises a membrane separation unit.

3. The process as described in claim 2, wherein said membrane separation unit contains a semi-permeable membrane having a molecular weight cut-off between about 500 and 2000 daltons.

4. The process as described in claim 2, wherein said miscella is passed in turbulent flow approximately parallel to the surface of the membrane of said membrane separation unit during said step (b).

5. The process as described in claim 1, wherein said step of contacting is at a temperature lower than about 60° C.

6. The process as described in claim 1, wherein said step of contacting is conducted in two stages at different temperatures, the temperature of the first stage being lower than about 60° C., and the temperature of the second stage being between about 60° C. and the normal boiling point of said miscella fraction.

7. The process as described in claim 1, wherein the ratio of said solvent to said plant material in said contacting step is between about 1:1 and 10:1 by weight.

8. The process as described in claim 1, wherein said step (a) is conducted in a counter-current extractor.

9. The process as described in claim 1, wherein said step (a) is conducted in a co-current extractor.

10. The process as described in claim 1, further comprising adiabatically transporting said miscella obtained from said step (a) to said separation unit.

11. The process as described in claim 10, wherein the temperature of said miscella is controlled within a range effective to maintain said miscella as a single phase.

12. The process as described in claim 1, further comprising the step of recycling said solvent in said second fraction from said step (b) for use in said step of contacting.

13. The process as described in claim 1, wherein said adsorbent is selected from the group consisting of silica and alumina.

14. The process as described in claim 1, further comprising the step of regenerating said adsorbent.

15. The process as described in claim 1, wherein said solvent is an aqueous solution of a lower monohydric aliphatic alcohol.

16. The process as described in claim 15, wherein said alcohol is selected from the group consisting of isopropyl alcohol, propyl alcohol, ethanol, methanol and mixtures thereof.

17. The process as described in claim 1, wherein said process is conducted in a continuous mode.

18. The process as described in claim 1, wherein said process is conducted in a batch mode.

* * * * *